US012589213B2

(12) United States Patent
Oddo et al.

(10) Patent No.: US 12,589,213 B2
(45) Date of Patent: *Mar. 31, 2026

(54) MECHANICAL VENTILATOR WITH NON-INVASIVE OPTION

(71) Applicant: Goldman Sephoric LLC, Santa Fe, NM (US)

(72) Inventors: Nicholas Leonard Oddo, Hilton Head Island, SC (US); Shane Woody, Mooresville, NC (US); Chad Josey, Mooresville, NC (US); Dylan Moore, Mooresville, NC (US)

(73) Assignee: Goldman Sephoric LLC, Santa Fe, NM (US)

( * ) Notice: Subject to any disclaimer, the term of this patent is extended or adjusted under 35 U.S.C. 154(b) by 44 days.

This patent is subject to a terminal disclaimer.

(21) Appl. No.: 17/858,261

(22) Filed: Jul. 6, 2022

(65) Prior Publication Data

US 2022/0370751 A1 Nov. 24, 2022

Related U.S. Application Data

(63) Continuation of application No. 16/996,067, filed on Aug. 18, 2020, now Pat. No. 11,400,250, which is a
(Continued)

(51) Int. Cl.
A61M 16/00 (2006.01)
A61M 16/04 (2006.01)
(Continued)

(52) U.S. Cl.
CPC .... *A61M 16/0057* (2013.01); *A61M 16/0003* (2014.02); *A61M 16/0063* (2014.02);
(Continued)

(58) Field of Classification Search
CPC .............. A61M 16/00; A61M 16/0003; A61M 16/0057; A61M 16/0063; A61M 16/0066;
(Continued)

(56) References Cited

U.S. PATENT DOCUMENTS 2,692,609 A 10/1954 Carter
2,944,627 A 7/1960 Skarstrom
(Continued)

FOREIGN PATENT DOCUMENTS

WO 2017/055995 A1 4/2017
WO 2019/180668 A1 9/2019
WO 2020/161471 A1 8/2020

OTHER PUBLICATIONS

John Z Chen et al., "Comparison of pulsed versus continuous oxygen delivery using realistic adult nasal airway replicas, "International Journal of COPD, p. 2559-2571, Aug. 24, 2017.
(Continued)

*Primary Examiner* — Joseph D. Boecker
(74) *Attorney, Agent, or Firm* — MEDLER FERRO WOODHOUSE & MILLS PLLC

(57) ABSTRACT

A ventilator includes a bidirectional breath detection airline and a flow outlet airline. The flow outlet airline includes an airline outlet. The flow outlet airline is configured to be connected to an invasive ventilator circuit or a noninvasive ventilator circuit. The breath detection airline includes airline inlet. The airline inlet is separated from the airline outlet of the flow outlet airline. The ventilator further includes a pressure sensor in direct fluid communication with the breath detection airline. The pressure sensor is configured to measure breathing pressure from the user and generate sensor data indicative of breathing by the user. The ventilator further includes a controller in electronic communication with the pressure sensor. The controller is programmed
(Continued)

to detect the breathing by the user based on the sensor data received from the pressure sensor.

20 Claims, 4 Drawing Sheets

Related U.S. Application Data continuation-in-part of application No. 16/704,413, filed on Dec. 5, 2019, now Pat. No. 10,946,161.

(60) Provisional application No. 63/047,742, filed on Jul. 2, 2020, provisional application No. 62/775,733, filed on Dec. 5, 2018.

(51) Int. Cl.

| | |
|---|---|
| *A61M 16/08* | (2006.01) |
| *A61M 16/10* | (2006.01) |
| *A61M 16/12* | (2006.01) |
| *A61M 16/20* | (2006.01) |
| *B01D 53/047* | (2006.01) |

(52) U.S. Cl.
CPC .... *A61M 16/0066* (2013.01); *A61M 16/0093* (2014.02); *A61M 16/024* (2017.08); *A61M 16/026* (2017.08); *A61M 16/101* (2014.02); *A61M 16/125* (2014.02); *A61M 16/20* (2013.01); *A61M 16/203* (2014.02); *B01D 53/047* (2013.01); *B01D 53/0476* (2013.01); *A61M 2016/0027* (2013.01); *A61M 2016/0039* (2013.01); *A61M 16/04* (2013.01); *A61M 16/0833* (2014.02); *A61M 16/0875* (2013.01); *A61M 16/1065* (2014.02); *A61M 16/201* (2014.02); *A61M 2205/3334* (2013.01); *A61M 2205/42* (2013.01); *B01D 2257/102* (2013.01); *B01D 2259/40009* (2013.01)

(58) Field of Classification Search
CPC ........... A61M 16/0069; A61M 16/024; A61M 16/026; A61M 16/04; A61M 16/0833; A61M 16/0875; A61M 16/0883; A61M 16/0891; A61M 16/101; A61M 16/125; A61M 16/127; A61M 16/20; A61M 16/201; A61M 16/202; A61M 16/203; A61M 2016/0027; A61M 2016/0033
See application file for complete search history.

(56) References Cited

U.S. PATENT DOCUMENTS

| | | | |
|---|---|---|---|
| 2,972,345 | A | 2/1961 | Spigel |
| 3,155,468 | A | 11/1964 | Montgareuil et al. |
| 3,537,449 | A | 11/1970 | Foxwell et al. |
| 3,990,442 | A | 11/1976 | Patneau |
| 4,044,763 | A | 8/1977 | Bird |
| 4,194,892 | A | 3/1980 | Jones et al. |
| 4,354,859 | A | 10/1982 | Keller, II et al. |
| 4,534,346 | A | 8/1985 | Schlaechter |
| 4,932,402 | A | 6/1990 | Snook et al. |
| 4,957,107 | A | 9/1990 | Sipin |
| 5,032,150 | A | 7/1991 | Knaebel |
| 5,048,515 | A | 9/1991 | Sanso |
| 5,161,525 | A | 11/1992 | Kimm et al. |
| 5,237,987 | A | 8/1993 | Anderson et al. |
| 5,280,780 | A | 1/1994 | Abel |
| 5,331,995 | A | 7/1994 | Westfall et al. |
| 5,370,728 | A | 12/1994 | LaSala et al. |
| 5,518,526 | A | 5/1996 | Baksh et al. |
| 5,605,148 | A | 2/1997 | Jones |
| 5,658,371 | A | 8/1997 | Smolarek et al. |
| 5,664,562 | A | 9/1997 | Bourdon |
| 5,664,563 | A | 9/1997 | Schroeder et al. |
| 5,882,380 | A | 3/1999 | Sircar |
| 5,918,597 | A | 7/1999 | Jones et al. |
| 5,997,611 | A | 12/1999 | Doong et al. |
| 6,116,242 | A | 9/2000 | Frye et al. |
| 6,146,447 | A | 11/2000 | Sircar et al. |
| 6,171,371 | B1 | 1/2001 | Derive et al. |
| 6,311,719 | B1 | 11/2001 | Hill et al. |
| 6,425,938 | B1 | 7/2002 | Xu et al. |
| 6,484,721 | B1 | 11/2002 | Bliss |
| 6,506,234 | B1 | 1/2003 | Ackley et al. |
| 6,584,973 | B1 | 7/2003 | Biondi et al. |
| 6,684,879 | B1 | 2/2004 | Coffee et al. |
| 6,752,152 | B2 | 6/2004 | Gale et al. |
| 6,802,889 | B2 | 10/2004 | Graham et al. |
| 6,811,590 | B2 | 11/2004 | Lee et al. |
| 6,949,133 | B2 | 9/2005 | McCombs et al. |
| 7,250,073 | B2 | 7/2007 | Keefer et al. |
| 7,794,522 | B2 | 9/2010 | Bliss et al. |
| 8,016,925 | B2 | 9/2011 | McCombs et al. |
| 8,025,059 | B2 | 9/2011 | Reissmann |
| 8,192,526 | B2 | 6/2012 | Zhong et al. |
| 8,337,599 | B2 | 12/2012 | Kiritake |
| 8,459,262 | B2 | 6/2013 | Ahlmèn et al. |
| 8,522,780 | B2 | 9/2013 | DeVries et al. |
| 8,568,519 | B2 | 10/2013 | Taylor et al. |
| 8,677,998 | B2 | 3/2014 | Yamaura et al. |
| 8,888,902 | B2 | 11/2014 | Galbraith et al. |
| 8,894,751 | B2 | 11/2014 | Galbraith et al. |
| 9,097,361 | B1 | 8/2015 | Ratner |
| 9,427,537 | B2 | 8/2016 | Zaiser et al. |
| 9,649,465 | B2 | 5/2017 | Wilkinson et al. |
| 9,649,589 | B2 | 5/2017 | Vemula et al. |
| 9,724,017 | B2 | 8/2017 | Baloa et al. |
| 9,839,757 | B2 | 12/2017 | Galbraith |
| 9,974,919 | B2 | 5/2018 | Richard et al. |
| 10,046,134 | B2 | 8/2018 | Devries et al. |
| 10,226,201 | B2 | 3/2019 | Ahmad et al. |
| 10,245,406 | B2 | 4/2019 | Devries et al. |
| 10,265,486 | B2 | 4/2019 | Allum et al. |
| 10,315,002 | B2 | 6/2019 | Devries et al. |
| 10,369,320 | B2 | 8/2019 | Ahmad et al. |
| 10,500,359 | B2 | 12/2019 | Schwaibold et al. |
| 10,792,449 | B2 | 10/2020 | Brambilla et al. |
| 10,799,663 | B1 | 10/2020 | Oddo et al. |
| 10,946,161 | B2 | 3/2021 | Oddo et al. |
| 11,135,392 | B2 | 10/2021 | Oddo et al. |
| 11,229,763 | B2 | 1/2022 | Oddo et al. |
| 11,359,733 | B2 | 6/2022 | Oddo et al. |
| 11,400,250 | B2 * | 8/2022 | Oddo ................ B01D 53/0454 |
| 2002/0053345 | A1 | 5/2002 | Jafari et al. |
| 2002/0185127 | A1 | 12/2002 | Melker et al. |
| 2003/0168062 | A1 | 9/2003 | Blythe et al. |
| 2003/0180164 | A1 | 9/2003 | Bunner et al. |
| 2004/0079360 | A1 | 4/2004 | Coffee et al. |
| 2004/0211422 | A1 | 10/2004 | Arcilla et al. |
| 2005/0039748 | A1 * | 2/2005 | Andrieux .............. A61M 16/10 128/204.22 |
| 2005/0103346 | A1 | 5/2005 | Noble |
| 2006/0048781 | A1 | 3/2006 | Nawata |
| 2006/0102181 | A1 | 5/2006 | McCombs et al. |
| 2006/0117957 | A1 | 6/2006 | McCombs et al. |
| 2006/0118189 | A1 | 6/2006 | Tekulve et al. |
| 2006/0249153 | A1 * | 11/2006 | DeVries .............. F04C 29/0035 128/205.24 |
| 2007/0000494 | A1 | 1/2007 | Banner et al. |
| 2007/0027375 | A1 | 2/2007 | Melker et al. |
| 2007/0125377 | A1 | 6/2007 | Heinonen et al. |
| 2008/0105258 | A1 | 5/2008 | Deane et al. |
| 2008/0121232 | A1 | 5/2008 | Cewers |
| 2008/0178882 | A1 * | 7/2008 | Christopher ...... A61M 16/0465 128/204.23 |
| 2008/0264412 | A1 | 10/2008 | Meyer et al. |
| 2009/0032130 | A1 | 2/2009 | Dumas et al. |
| 2009/0071333 | A1 | 3/2009 | LaBuda et al. |
| 2009/0078256 | A1 | 3/2009 | Armitstead et al. |
| 2009/0199855 | A1 * | 8/2009 | Davenport ........ A61M 16/0677 128/204.23 |

(56)  References Cited

U.S. PATENT DOCUMENTS

| | | | |
|---|---|---|---|
| 2009/0229460 A1 | 9/2009 | McClain et al. | |
| 2009/0260625 A1 | 10/2009 | Wondka | |
| 2010/0051029 A1* | 3/2010 | Jafari | A61M 16/0051 |
| | | | 128/204.23 |
| 2010/0078024 A1* | 4/2010 | Andrieux | A61M 16/201 |
| | | | 128/204.21 |
| 2011/0180063 A1 | 7/2011 | Hunsicker et al. | |
| 2011/0197887 A1* | 8/2011 | Truschel | A61M 16/024 |
| | | | 128/204.23 |
| 2012/0017909 A1 | 1/2012 | Porges et al. | |
| 2012/0065522 A1 | 3/2012 | Lewicke | |
| 2012/0065533 A1 | 3/2012 | Carrillo et al. | |
| 2012/0128549 A1 | 5/2012 | Zhou et al. | |
| 2012/0192862 A1 | 8/2012 | Lewis et al. | |
| 2012/0192864 A1 | 8/2012 | Galbraith et al. | |
| 2013/0136638 A1 | 5/2013 | Foerster | |
| 2013/0146053 A1 | 6/2013 | Mazela et al. | |
| 2013/0184619 A1 | 7/2013 | Von et al. | |
| 2013/0206144 A1* | 8/2013 | Ahmad | A61M 16/0858 |
| | | | 128/204.23 |
| 2013/0276634 A1 | 10/2013 | McKenna et al. | |
| 2014/0014103 A1 | 1/2014 | Smaldone et al. | |
| 2014/0137744 A1 | 5/2014 | Wilkinson et al. | |
| 2014/0216453 A1 | 8/2014 | Whitcher | |
| 2014/0261426 A1* | 9/2014 | Ahmad | A61M 16/026 |
| | | | 128/204.23 |
| 2014/0283833 A1 | 9/2014 | Zheng et al. | |
| 2014/0346380 A1 | 11/2014 | Bourqui | |
| 2015/0000664 A1 | 1/2015 | Desilva et al. | |
| 2015/0040904 A1 | 2/2015 | Nitta | |
| 2015/0120067 A1 | 4/2015 | Wing et al. | |
| 2015/0231350 A1* | 8/2015 | Baloa Welzien | A61M 16/0069 |
| | | | 128/204.23 |
| 2015/0273174 A1 | 10/2015 | Hart et al. | |
| 2015/0328417 A1 | 11/2015 | Löser et al. | |
| 2016/0193438 A1 | 7/2016 | White et al. | |
| 2017/0119279 A1 | 5/2017 | Ahmad et al. | |
| 2017/0119280 A1 | 5/2017 | Ahmad et al. | |
| 2017/0143932 A1 | 5/2017 | Mccarthy et al. | |
| 2017/0224251 A1 | 8/2017 | Ahmad et al. | |
| 2017/0319800 A1 | 11/2017 | Richards | |
| 2018/0001042 A1 | 1/2018 | Albanese et al. | |
| 2018/0056024 A1 | 3/2018 | Harrington et al. | |
| 2018/0071468 A1 | 3/2018 | Dennis et al. | |
| 2018/0221608 A1* | 8/2018 | Schwaibold | A61M 16/024 |
| 2018/0304031 A1 | 10/2018 | Havercroft et al. | |
| 2018/0344919 A1 | 12/2018 | Jones et al. | |
| 2019/0099570 A1 | 4/2019 | Brambilla et al. | |
| 2019/0217030 A1 | 7/2019 | Burgess et al. | |
| 2019/0261891 A1 | 8/2019 | Ahmad et al. | |
| 2020/0121877 A1 | 4/2020 | Albanese et al. | |
| 2020/0139072 A1 | 5/2020 | Zapol et al. | |
| 2020/0147338 A1 | 5/2020 | Lacey | |
| 2020/0188615 A1 | 6/2020 | Troili | |
| 2020/0368482 A1 | 11/2020 | Westfall et al. | |
| 2021/0001075 A1 | 1/2021 | Oddo et al. | |
| 2021/0038856 A1 | 2/2021 | Oddo et al. | |
| 2021/0048112 A1 | 2/2021 | Oddo et al. | |
| 2021/0338954 A1 | 11/2021 | Glaw et al. | |
| 2021/0386291 A1 | 12/2021 | Oddo et al. | |
| 2021/0386959 A1 | 12/2021 | Oddo et al. | |
| 2022/0096781 A1 | 3/2022 | Dong et al. | |
| 2022/0296846 A1 | 9/2022 | Liu | |

OTHER PUBLICATIONS

E.M. Kopaygordodsky et al., "Predictive Dynamic Model of Single-Stage Ultra-Rapid Pressure Swing Adsorption," AlChE Journal, p. 953-962, vol. 50, No. 5, May 2004, published online in Wiley InterScience (www.interscience.wiley.com).

V. Rama Rao et al., "Design of a Two-Step Pulsed Pressure-Swing Adsorption-Based Oxygen Concentrator," AlChE Journal, p. 354-370, vol. 56, No. 2, Feb. 2010, published online Aug. 13, 2009 in Wiley InterScience (www.interscience.wiley.com).

F. Rezaei et al., "Structured adsorbents in has separation processes", Separation and purification Technology Journal, p. 243-256, 2009, journal homepage: www.elsevier.com/locate/seppur.

Matthew d. Urish et al., Multivariable Model Predictive Control of a Novel Rapid Pressure Swing Adsorption System, AlCHE JOurnal, p. 1234-1245, vol. 64, No. 4, Apr. 2018, published online Nov. 2, 2017 in Wiley Online Library (wileyonlinelibrary.com).

International Search Report received for PCT Patent Application No. PCT/US2021/046418, mailed on Dec. 9, 2021, 8 pages.

* cited by examiner

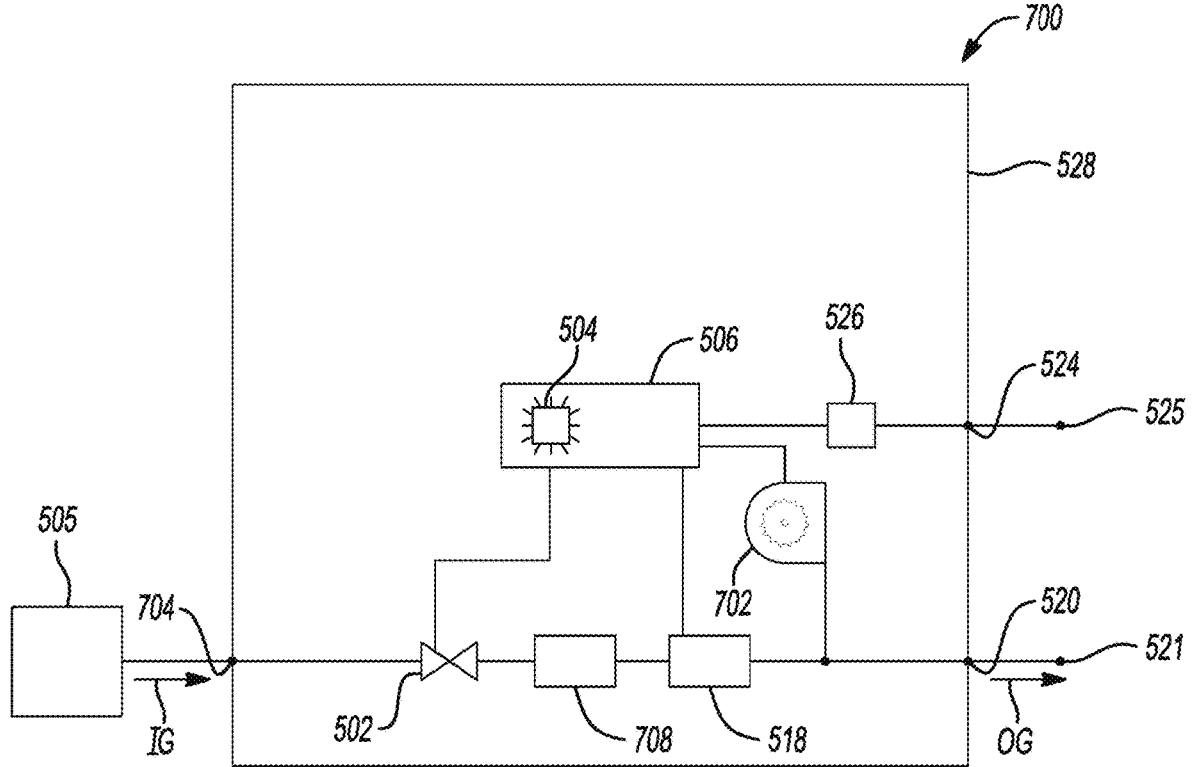
$$Fig-3C$$

MECHANICAL VENTILATOR WITH NON-INVASIVE OPTION

CROSS-REFERENCE TO RELATED APPLICATIONS

This application is a continuation of U.S. patent application Ser. No. 16/996,067, filed Aug. 18, 2020, and titled "MECHANICAL VENTILATOR WITH NON-INVASIVE OPTION", which claims priority, and the benefit of, U.S. Provisional Patent Application 63/047,742, filed Jul. 2, 2020, U.S. patent application Ser. No. 16/704,413, filed on Dec. 5, 2019, which in turn claims priority, and the benefit of, U.S. Provisional Patent Application 62/775,733, filed on Dec. 5, 2018, each of which is hereby incorporated by reference in its entirety.

TECHNICAL FIELD

The present disclosure generally relates to a medical device, and more particularly, to a non-invasive ventilator.

BACKGROUND

Conventional ventilators can lack portability and require continuous monitoring of user condition and manual adjustment of ventilator settings by health care personnel. In many cases, expensive ventilation monitoring technologies such as CO2 capnography must be used in conjunction with a conventional ventilator, to determine effectiveness and make adjustments in settings during use. Conventional ventilator control methodology and ventilator configuration is not readily adaptable for ventilator use with certain user conditions, for example, when the user is talking, during sleep, or when the user is connected to Continuous Positive Airway Pressure (CPAP) and/or Bilevel Positive Airway Pressure (BiPAP) machines, for example, during sleep apnea therapy.

SUMMARY

A ventilator includes a tubing configured to receive an input gas and a flow outlet airline in fluid communication with the tubing. The flow outlet airline includes an airline outlet, and the flow outlet airline is configured to supply an output gas to a user via the airline outlet. The ventilator further includes a breath detection airline including an airline inlet, wherein the airline inlet is separated from the airline outlet of the flow outlet airline. The breath detection airline is configured to receive breathing gas from the user during exhalation by the user via the airline inlet. The ventilator further includes a pressure sensor in direct fluid communication with the breath detection airline. The pressure sensor is configured to measure breathing pressure from the user, and the pressure sensor is configured to generate sensor data indicative of breathing by the user. The ventilator further includes a controller in electronic communication with the pressure sensor. The controller is programmed to detect the breathing by the user based on the sensor data received from the pressure sensor. The flow outlet airline is configured to be connected to an invasive ventilator circuit or a noninvasive ventilator circuit.

The above features and advantages and other features and advantages of the present teachings are readily apparent from the following detailed description of the modes for carrying out the present teachings when taken in connection with the accompanying drawings.

BRIEF DESCRIPTION OF THE DRAWINGS

The accompanying drawings, which are incorporated into and constitute a part of this specification, illustrate implementations of the disclosure and together with the description, serve to explain the principles of the disclosure.

FIG. 3C is a schematic illustration of a ventilator that uses an oxygen concentrator.

FIG. 6 is a schematic diagram of an invasive ventilator circuit using a breathing tube, an adapter, and an oxygen tubing.

FIG. 7 is a schematic diagram of a ventilator with an internal oxygen concentrator that allows the use of an external gas source.

FIG. 8 is a schematic diagram of a ventilator that can function as BiPAP or CPAP device, an $O_2$ concentrator, and/or ventilator with different modes.

FIG. 9 is a schematic diagram of a ventilator than can use a pulse dose oxygen concentrator as an $O_2$ source.

DETAILED DESCRIPTION

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property can include additional elements not having that property.

Figures 1, 2:
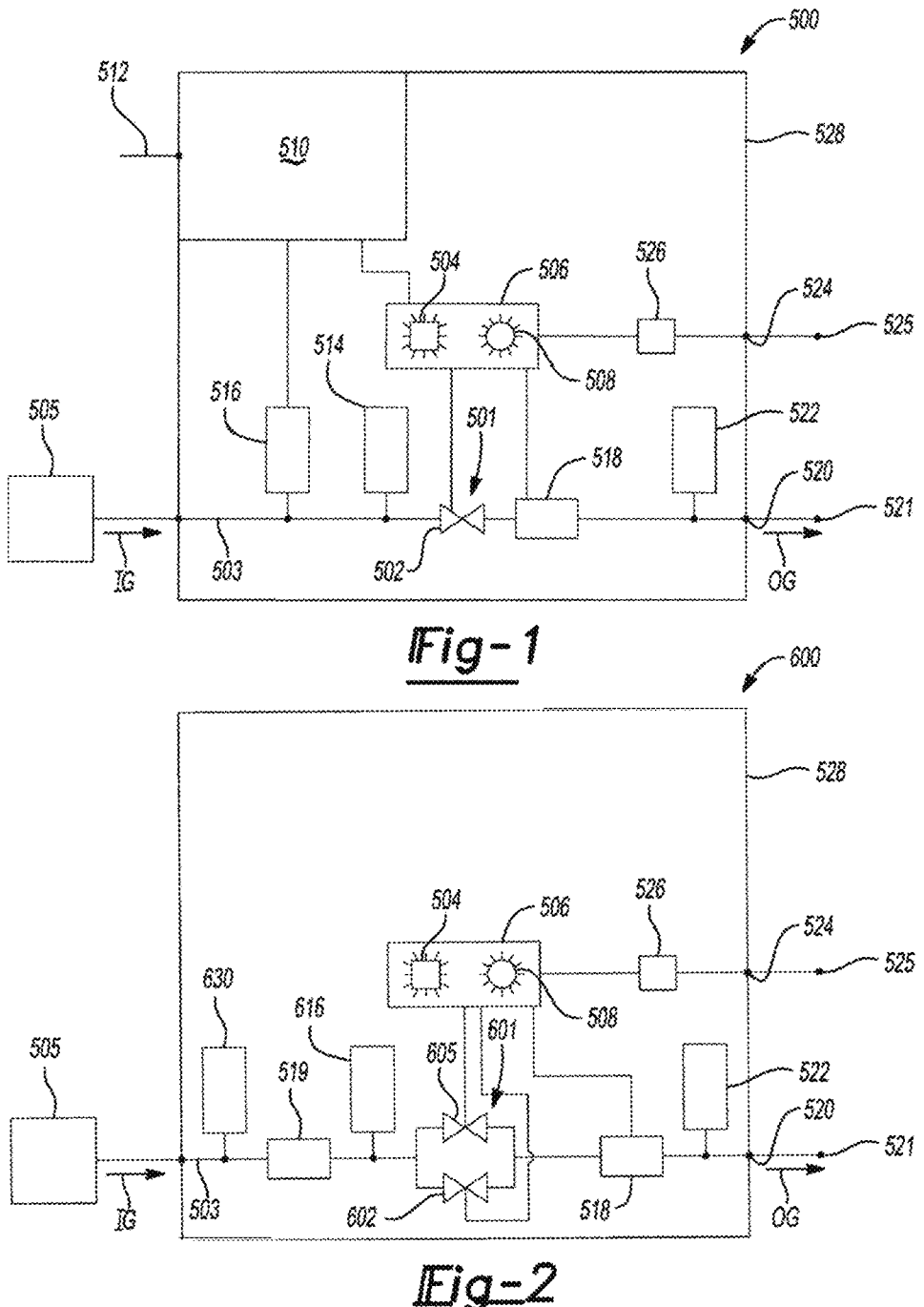
FIG. 1 is a schematic illustration of a ventilator with an on-off solenoid valve to modulate a compressed or oxygen source.
FIG. 2 is a schematic illustration of a ventilator with proportional control valves and an air volume tank to modulate high pressure or low pressure oxygen or compressed air source, wherein the ventilator is configured to detect a high pressure or low pressure oxygen source from a single input airline using two proportional control valves and modulate the output gas.

With reference to FIG. 1, a ventilator 500 includes a ventilator tubing 503 and a valve 502 in fluid communication with the ventilator tubing 503. The ventilator tubing 503 is configured to receive input gas IG from a compressed oxygen source and/or an air source (i.e., the input gas source 505), and the valve 502 is configured to modulate the compressed oxygen or air sources received from the input gas source The valve 502 is downstream of the input gas source 505 and can be a solenoid valve and has at least an open state and a closed state. The valve 502 can be part of a valve arrangement 501. The valve arrangement 501 can therefore include one or more of the valves 502 (e.g., solenoid valves). It is also contemplated that the valve arrangement 501 can include other types of valves. Hence, the ventilator 500 can include a single valve 502 (e.g., a single solenoid valve) to minimize cost and weight. Alternatively, the ventilator 500 can include more than one valve 502. The ventilator 500 functions by receiving input gas IG from the input gas source through a ventilator tubing 503. As non-limiting examples, the input source can be an air compressor, air blower, stationary oxygen concentrator, portable oxygen concentrator, air tank, and/or oxygen tank. A continuous flow of the input gas IG enters the ventilator 500 through the ventilator tubing 503, and when the valve 502 opens, the flow rate of the input gas IG and the output gas OG is the same or at least substantially the same.

The ventilator 500 further includes a controller 504, such as a microprocessor or a microcontroller unit. The controller 504 can additionally include (or be connected to) a non-transitory memory capable of storing data. The ON-OFF cycles of the valve 502 are controlled using a controller 504, such as a microprocessor or microcontroller unit. The controller 504 can be part of an electronic board 506, which can contain additional electronic components including but not limited to: power electronics, resistors, capacitors, alarms 508, and copper traces. The electronic board 506 can include one or more alarms 508. The alarms 508 can be, for example, used to warn the user of one or more of the following conditions: tubing disconnections, electrical or air supply failure, high peak airway pressure, auto-positive end-expiratory pressure (auto-PEEP), high gas supply pressures, and/or no spontaneous breathing. Further, this electronic board 506 can be utilized as a battery management system for a portable ventilator device that is battery powered.

The ventilator 500 can include an electrical power source 510, such as a portable rechargeable Li-Ion battery pack or another suitable portable battery assembly. The electrical power source 510 (e.g., battery pack) can include a recharging interface 512, such as a port or cable, thereby allowing the electrical power source 510 to be recharged. As non-limiting examples, the recharging interface 512 can be a Universal Serial Bus-C (USB-C), a USB, a micro-USB, or other charging interfaces. The electrical power source 510 can be electrically connected to the electronic board 506 to supply electricity to the controller 504 and the alarms 508.

This controller 504 can be in the form of an field programmable gate array (FPGA), microcontroller unit (MCU), single board computer, application-specific integrated circuit (ASIC), programmable logic controller (PLC) on a chip, and/or other processing or computer hardware that can control the ON/OFF or OPEN/CLOSE cycles of a solenoid valve 502. The valve 502 (e.g., solenoid valve) can be controlled using fluidic chips or other non-conventional or pneumatic methods of valve control, such as air cylinder actuations. To this end, the ventilator 500 can include a pneumatic actuator 514, such as an air cylinder or pressure actuator. For example, instead of an electronically controlled valve (e.g., valve 502), the ventilator 500 can include the pneumatic actuator 514 and a check valve (e.g., valve 502). Thus, the valve 502 can be a check valve. As such, the cracking pressure of the check valve (e.g., valve 502) is higher than the pressure of the input gas IG and, therefore, the check valve (e.g., valve 502) can only be opened using the pneumatic actuator (e.g., an air cylinder or pressure actuator) For this reason, the valve 502 is downstream of the pneumatic actuator 514. The pneumatic actuator 514 (e.g., air cylinder or pressure actuator) can be electronically controlled to open at the beginning or end of the respiration cycle (i.e., at inhalation) to provide a ventilatory inspiratory positive airway pressure (IPAP) or positive end-expiratory pressure (PEEP). In other words, the controller 504 can be programmed to command the pneumatic actuator 514 to open at inhalation of the user. This can be beneficial in situations where very low-pressure oxygen or compressed air sources are used, and where miniature electronically controlled solenoid valves have small orifices (e.g., about 0.009 inches diameter) would not be effective. The miniature solenoid valves create significant orifice/flow restrictions that necessitate the use of high-pressure input gas sources, in the range of 25-50 pounds per square inch (PSI). Check valves, on the other hand, generally have much larger orifices, such as 0.75 inch diameter, in small size form factors compared to the electronically controlled valve counterparts. For example, a 7 mm orifice electronically controlled solenoid valve weighs about 1 pound and consumes approximately 13 W of power, which would make the ventilator 500 bulky. By contrast, the ventilator 500 including the pneumatic actuator 514 can rival a miniature electronically controlled solenoid valve 502 in terms of weight and power consumption, while having larger orifices and allow the use of lower pressure gas sources than in other systems. Any numbers provided above or below are only examples and should not be interpreted as functional limitations of the presently disclosed ventilator 500.

The ventilator 500 can include an oxygen or air tank 516, which is configured as a pressure source to deliver pressurized oxygen to the patient for ventilatory support. The electrical power source 510 can be electrically connected to the oxygen tank 516 and the electric board 506. However, the ventilator 500 can be completely pneumatically powered. As such, a certain portion of the input gas IG can be used to drive an impeller, which can generate electrical energy that can power the controller 504 and other energy consuming components such as the valve 502. However, other oxygen and/or pressure sources can be utilized such as continuous flow oxygen concentrators or air compressors. In other words, the input gas source 505 can be an air compressor, an oxygen source, a pressure source, a continuous flow oxygen concentrator and/or an air compressor. Further, flow control software and the hardware of the valve 502 (e.g., solenoid valve) can be utilized such that gas sources with different pressure values can be interchanged while maintaining a consistent or dynamically adjusted controlled gas flow rate to the patient. As discussed above, the pneumatic actuator 514, such as a pressure actuator, can be integrally built into the ventilator 500, allowing a pulse dose oxygen concentrator to be utilized. This pneumatic actuator 514 can periodically trigger a pulse dose oxygen conserver at a fixed rate, such as once every 4 seconds or 15 "breaths per minute". The pulse dose oxygen bursts would accumulate inside an air volume tank 516 connected to or disposed inside the ventilator 500. For this reason, the tank 516 is upstream of the pneumatic actuator 514. The ventilator 500 then outputs the oxygen pulse from the air volume tank 516 in a manner that ventilatory support would be provided the patient.

The ventilator 500 can have two modes of operation, namely: (1) an oxygen conserver mode; and 2) ventilator mode. The ventilator mode can also have ventilator submodes of operation. These ventilation submodes can be selected by the patient, physician, and/or manufacturer and can include assist control, tidal assist ventilation, and/or synchronized intermittent mandatory ventilation (SIMV). The pressurized output gas OG can be outputted in a plurality of different waveforms, such as descending ramp, ascending ramp, sinusoidal, and/or square wave form, among others. Further, these ventilator gas output waveforms and flow rates can be adjusted based on breathing airway pressure and/or flow measurements from a second lumen air line. In the presently disclosed ventilator 500, the flow control and breathing measurements are separately obtained via dual lumen airlines (i.e., flow outlet airline 520 and breath detection airline 524). This dual lumen airline setup prevents electrical signal interference and saturation of the gas output pressure/flow and the breathing measurement pressure/flow sensor sensors found in prior art oxygen conserving devices and ventilators. Further, this also allows for the use of much more sensitive pressure sensors for detecting breathing. In other mechanical ventilators, single lumen tubes are used and, as such, the flow output and breath "triggering" or detection are done in the same airline. Further, in other mechanical ventilators, only inhalation is detected. In other mechanical ventilators, exhalation and inhalation berating flows are spearhead using one-way check valves which comprise the dual limb ventilator circuit. In the mechanical ventilators (e.g., ventilator 500) of the present disclosure, the proximal pressure line is bidirectional (i.e., there are no check valves and therefore the flow is a bidirectional flow BG) and, as such, there is no pressure or flow "triggers" but rather patterns in breathing are mathematically computed based on nasopharynx pressure and/or breath detection sensor waveforms. In experimental use, by positioning the pressure sensors for breath detection in a separate lumen from the lumen used for gas output, it was found six times (6x) more sensitive pressure sensors can be utilized with a dual lumen setup for detecting breathing compared to single lumen pressure sensors. The ventilator 500 can also have rest, exercise, and/or sleep settings.

The ventilator 500 can further include a flow outlet airline 520 and a flow sensor 518 to measure the flow rate of this continuous gas output OG to the patient. The flow outlet airline 520 and the flow sensor 518 are in fluid communication with the tubing 503. The flow sensor 518 is downstream of the tank 516, the valve 502, and the pneumatic actuator 514 to precisely measure the flow rate of the output gas OG being supplied to the user of the ventilator 500. This flow sensor 518 can comprise a plurality of sensor methodologies. For example, the flow sensor 518 can utilize the thermo-transfer principle, also known as the calorimetric principle, to measure large ranges of gas flow rates when the gain factor of the flow sensor 518 is specifically calibrated and tested, such that the sensor output is amplified and two point trimmed at zero flow as well as a secondary flow rate point to optimize linearity within a certain flow rate range, such as 0-40 standard liter per minute (SLPM) gas flow. Under this thermo-transfer principle, inside the flow sensor 518, a temperature sensor (not shown) is heated periodically by a heater element (not shown). The flowing gas absorbs heat energy and conducts it away. The resulting temperature change is an indication of flow, which translates to an analog voltage value that is then correlated to a flow output curve based on experimental data from the original equipment manufacturer (OEM) or sensor manufacturer during calibration and/or testing. Generally, this flow sensor 518 is a flow-through type sensor, wherein the flow sensor 518 includes a barb fitting inlet that connects to the oxygen or tubing 503, as well as a barb outlet to the flow outlet airline 520 with minimal resistance of fluidic loss. This flow outlet airline 520 can connect to a 22 mm breathing tube, hose barb, adapter, or other tubing connection thereafter. The flow sensor 518 can alternatively be other types of sensor, such as: turbine-type flow meters, rotometers, and membrane based differential pressure and temperature sensors that can be used to calculate flow rates, which can work especially well for laminar type or large volume/low pressure flows. the flow outlet airline 520 includes an airline outlet 521. Further, this flow outlet airline 520 can also be fluidly coupled to an air entrainment device 522. The air entrainment device 522 can be a conduit including a jet nozzle, a conduit having a Venturi shape, a conduit using the Coanda effect, a conduit using the Jet Principle effect and/or another conduit specifically configured entrain a flow of gas. To properly entrain a flow of gas delivered to the user of the ventilator 500, the air entrainment device 522 is disposed downstream of the tank 516, the pneumatic actuator 514, the valve 502, and the flow sensor 518.

In certain embodiments, while using the oxygen or air tank 516, a bolus or partial bolus of oxygen or compressed air can be output to the patient at the beginning of their inspiration or end of their expiration. The peak inspiratory flow demands are the highest, potentially maximizing effective gas exchange in the lungs. This flow rate output from an air or oxygen tank 516 is not directly controlled, but rather is determined based on the orifice size/flow restriction of the solenoid valve 502 at a certain pressure. For example, with a 10 PSIG pressure gas source in the air or oxygen tank 516, the output flow rate through a 0.009 inch diameter orifice electronically controlled solenoid valve 502 in a completely open state would be 30 liters per minute (LPM), and with a 50 PSIG pressure gas source in the air or oxygen tank 616, the flow rate output would be 100 LPM. After the bolus volume, for example 50 mL at a flow rate of 30 LPM, from the air or oxygen tank 516 is outputted to a user through the flow outlet airline 520, a continuous flow of input gas IG from the input gas source, for example 2 LPM, until the end of the useful phase of respiration such as 70% inhalation time, can follow. Then, the electronically controlled solenoid valve 502 closes.

During operation, user spontaneous breathing is detected using a separated breath detection airline 524 and an ultra-sensitive pressure sensor for measuring breathing pressures (e.g., nasopharynx pressure). No check valves are in fluid communication with the breath detection airline 524. Accordingly, the breath detection airline 524 allows bidirectional flow to maximize the accuracy of the pressure sensor 526. The breath detection airline 524 includes an airline inlet 525. The airline inlet 525 is separated from the airline outlet 521 of the flow outlet airline 520 to minimize interference and therefore maximize the accuracy of the pressure sensor 526. The pressure sensor 526 is in direct fluid communication with the breath detection airline 524 to maximize its accuracy. This breath detection airline 524 is configured to be fluidly connected to a 22 mm breathing tube, hose barb, adapter, or other tubing connection. The breath detection airline 524 is not in fluid communication with the flow outlet airline 520 to maximize the accuracy of the pressure sensor 526. By fluidly separating the airline inlet 525 of the breath detection airline 524 from the airline outlet 521 of the flow outlet airline 520, breathing pressures (e.g., nasopharynx pressures) from a user of the ventilator 500 can be measured without signal interference from the pressure/flow output from the ventilator 500, which would otherwise saturate the ultra-sensitive pressure sensor 526 required to measure the breathing pressures (e.g., nasopharynx pressures). In other ventilators and oxygen concentrators, a single airline is generally utilized in which a flow or pressure trigger threshold, ex. −0.13 cm $H_2O$ pressure, is used to determine the start of inhalation. This generally creates substantial lag in the ventilator gas output or false breathing triggers. Further, this necessitates the use of far less sensitive pressure sensors to prevent the pressure sensor from getting saturated from the output flow gas from the ventilator. Also, if flow is triggered based on a flow ramp, there can still exist substantial signal interference using a single airline.

In the presently disclosed ventilator 500, a breath detection software is used to predict transitions in breathing states and breathing time states, for example: transition from inhale to exhale, 70% inhalation time, transition from exhale to inhale, predicted PEEP based on % of exhalation. This breath detection software functions by measuring nasopharynx pressures using a separated breath detection airline 524, then storing the voltage values from the pressure sensor 526 in the controller 504 (e.g., microcontroller), RAM or EEPROM. For this reason, the controller 504 is in electronic communication with the pressure sensor 526. Breath transition states and timing predictions are detected through one or more mathematical calculations involving the pressure sensor voltage data including but not limited to: data filtering, differentiation, integration, linear regression analysis and linearization, moving average calculations, Taylor series approximations, steady state error compensation, model predictive control, proportional control, fuzzy control theory, ODEs, radial basis functions, quadratic-program approximation, feedforward control, adaptive control, PI and/or PID control, SISO control schema, Laplace transformations. A moving average calculation can be used such that, if the filtered pressure sensor data falls below the moving average, a transition from an inhale to an exhale is predicted.

Other sensors can also be used independently, in combination with, or to replace the pressure sensor(s) 526 described herein to measure data trends in breathing, implement predictive breath detection software algorithms, and/or actuate at certain threshold values and/or ramps including but not limited to: flow sensors, $CO_2$ gas concentration sensors, $O_2$ gas concentration sensors, temperature sensors, humidity sensors, volume sensors, and/or acoustic sensors. This breath detection is used to determine when to output ventilator gas, which can include compressed air, oxygen, or a mixture thereof, to the patient at the correct time in order to provide pressure/ventilatory support, as well as facilitate effective lung gas exchange, ventilation, and manage arterial blood gases (ABGs) such as $PaCO_2$ and $PaO_2$. Accordingly, the pressure sensor 526 is configured to generate sensor data indicative of breathing by the user, and the controller 504 is programmed to detect the breathing of the user based on the sensor data received from the pressure sensor 526. The controller 504 is then programmed to command the ventilator 500 (through the valve 502, the tank 516, and/or pneumatic actuator 514) to provide a specific flow of the output gas OG to the patient based, at least on part, on the data collected from the pressure sensor 526. The pressure sensor 526 can be referred to as the breathing pressure sensor.

The components and electromechanical subassemblies of the ventilator 500 are contained within an electronics enclosure 528, which can be manufactured using a plurality of manufacturing methods including but not limited to: injection molding, 3D printing, CNC machining, sheet metal fabrication, PCBA, wire harnessing, and other manual or automated manufacturing techniques not described herein.

With reference to FIG. 2, a ventilator 600 is identical or at least substantially similar to the ventilator 500 described above, except for the features described below. The ventilator 600 includes one or more electronically controlled proportional control valves 602 and an air volume tank(s) 616. These proportional control valves 602 and air volume tanks 616 can be configured in numerous ways for different purposes. The proportional control valves 602 are part of a valve arrangement 601 and can be fluidly coupled in parallel. One or more proportional valves 602 can be used to output a high pressure or low pressure oxygen/compressed output gas OG. Further, the ventilator 600 can detect a high pressure or low pressure oxygen source from a single input airline (i.e., tubing 503) using a high pressure proportional control valve and a low pressure proportional control valve to modulate output gas OG. To do so, the ventilator 600 can include an input pressure sensor 630 to detect the pressure of the input gas IG originating from the input gas source 505, or by utilizing one proportional valve 602 in the fully open position for a short time period, such as 50 milliseconds, to determine the flow rate output detected by the flow sensor 518. The flow rate can be used to calculate the pressure of the input gas IG based on the orifice diameter/flow restriction of the electronically controlled proportional control valve 602. To maximize the accuracy of the input pressure sensor 630, the input pressure sensor 630 is upstream of the tank 616, the proportional valves 602, and the flow sensor 518.

When the proportional control valve(s) 602 are closed, the input gas IG of continuous flow can accumulate in the air volume tank 616. This can serve the following purposes: bolus output at the beginning of the useful phase of respiration, a method of conserving oxygen/compressed air, and/or a method for proportional flow control of the gas output, such that a high output flow rate (e.g., 200 LPM) can be outputted from a low input flow rate (e.g., 6 LPM). Depending on the application, the size/volume specifications of the air volume tank 616 will be different. For example, if oxygen conservation (e.g., when oxygen accumulates when the patient is exhaling) is the primary focus, a much larger air volume tank 616 should be sized and used in conjunction with proportional flow control. However, if the goal is just to output a bolus of oxygen at the beginning of inspiration or end of expiration during each breath with no proportional flow control, a much smaller air volume tank 616 should be sized, which can further enhance portability of the device but reduce oxygen conservation or high flow output capabilities. The use of proportional flow control is especially relevant for 50 PSIG high pressure gas sources, such as medical hospital oxygen wall supplies, where a large bolus of high-pressure gas can cause over-inflating of the lungs or barotrauma.

In addition to the flow sensor 518, the ventilator 600 can include a second flow sensor 519. Accordingly, the flow sensor 518 can be referred to as the first flow sensor or output flow sensor, and the second flow sensor 519 can be referred to as the input flow sensor. As such, the flow of the input gas IG can be measured using the second flow sensor 519. The second flow sensor 519 is upstream of the valve 502, and the first flow sensor 518 is downstream of the valve 502 to accurately measure the flow of the input gas IG and the output gas OG. The controller 504 can be programmed to maintain the input gas IG flow at a fixed oxygen conservation ratio (e.g., 3×), and the input gas IG can be accumulated in the air volume tank 616 when the proportional control valves 602 are closed. The flow of the input gas IG can be, for example, 2 LPM. Hence, a 6 LPM flow of gas would be outputted from the air volume tank 616, and one or more of the proportional control valves 602 would be open during the useful phase of respiration. This proportional flow control can utilize PI or PID control algorithms. The proportional gain Kp and integrator values of the PI or PID control algorithms can be, for example, experimentally determined and set by the manufacturer to have the smoothest and most accurate flow rate outputs at a given range. The proportional gain Kp and integrator values of the PI control can be automatically updated by the controller 504 based on different input flow conditions detected by the second flow sensor 519 as well as actual output flow detected by first flow sensor 518 vs predetermined output flow rates. The controller 504 can use feedback or feedforward control to compensate for error and maximize flow rate precision. The flow of the output gas OG to the user can be time controlled. For example, the duration of the flow of the output gas can be set to be a variable time, thereby suppling the output gas OG with variable volume/pressure profile based on user breathing times (e.g., 90% exhale time for start of flow and 70% of inhale time for end of flow). Alternatively, the output gas OG supplied to the user can be volume controlled, pressure controlled, flow controlled, or a combination therein. Further, the output gas OG does not necessarily need to be a square waveform, but rather can consist of different flow, pressure, and/or waveform patterns, which can be dynamically adjusted by the ventilator 600 on a breath by breath basis. Some of these waveform patterns can include descending ramp, sinusoidal, oscillatory, step functions, and/or a combination of waveforms thereof, which can also be generated using mathematical patterns based on sensor data and lung models programmed into the ventilator 600.

In this configuration, the oxygen conservation ratio is a fixed value. Alternatively, the flow rate of the output gas OG can be controlled by the user. In one example, the user can have a flow dial or knob that specifies a flow rate of the output gas OG of 4 LPM. As such, the oxygen conservation ratio would be algorithmically adjusted by a software program being run by the controller 504 based on the user input. This adjustment in output flow rate can be performed by the ventilator 600 based on computations involving one or more sensors (e.g., the pressure sensor 526 or external sensors or devices not contained in the ventilator 600). Sensors or devices that can be used to automatically adjust oxygen flow rate to the user include, but are not limited to, sensors or devices that measure the following, independently or in combination thereof: breathing flows, pressures, $O_2$ concentrations, $CO_2$ concentrations, humidity, acoustics/voice, temperature, trace gas or liquid concentrations, pulse oximetry, vital signs such as heart rate and/or blood pressure, and/or physical movement of the ventilator 600.

The ventilator 600 can include proportional pressure control valves instead of proportional flow control valves 602. This would be especially useful for pressure-controlled ventilators, as well as low pressure (i.e., less than 5 PSIG) input gas sources (i.e., input gas source 505) where the springs inside existing miniature electronically controlled proportional control valve designs are generally too stiff to precisely control the flow of low pressure gas. These pressure control valves generally function as closed-loop electronic air pressure regulators. Single and double loop pressure control valve architectures generally include two or more valves, a manifold, internal pressure transducer, and electronic controls (not shown). Output pressure is proportional to an electrical signal input. Pressure is controlled by two solenoid valves. One valve functions as the inlet control and the other as an exhaust. The pressure output is measured by a pressure transducer internal to the proportional pressure control valve system and provides a feedback signal to the electronic controls. This feedback signal is compared against the command signal input. A difference between the two signals causes one of the solenoid valves 602 to open allowing flow in or out of the system. Accurate pressure is maintained by controlling these two valves. By controlled pressure, the flow is slowed down and hence a maximum flow rate from the air volume tank 616 can be set that is lower than the flow rate that would be output from an air volume tank 616 and standard electronically controlled solenoid valve 602 that fully opens. With this proportional pressure control, the pressure output can be precisely controlled to reduce the risks of barotrauma or lung overinflation from the ventilator gas output. Flow control can also be executed indirectly by controlling pressure by measuring flow rates using the first flow sensor 518. The flow can be controlled, for example, by varying the times of the inlet control and exhaust timings of the valves in the proportional pressure control system.

Figures 3A, 3B:
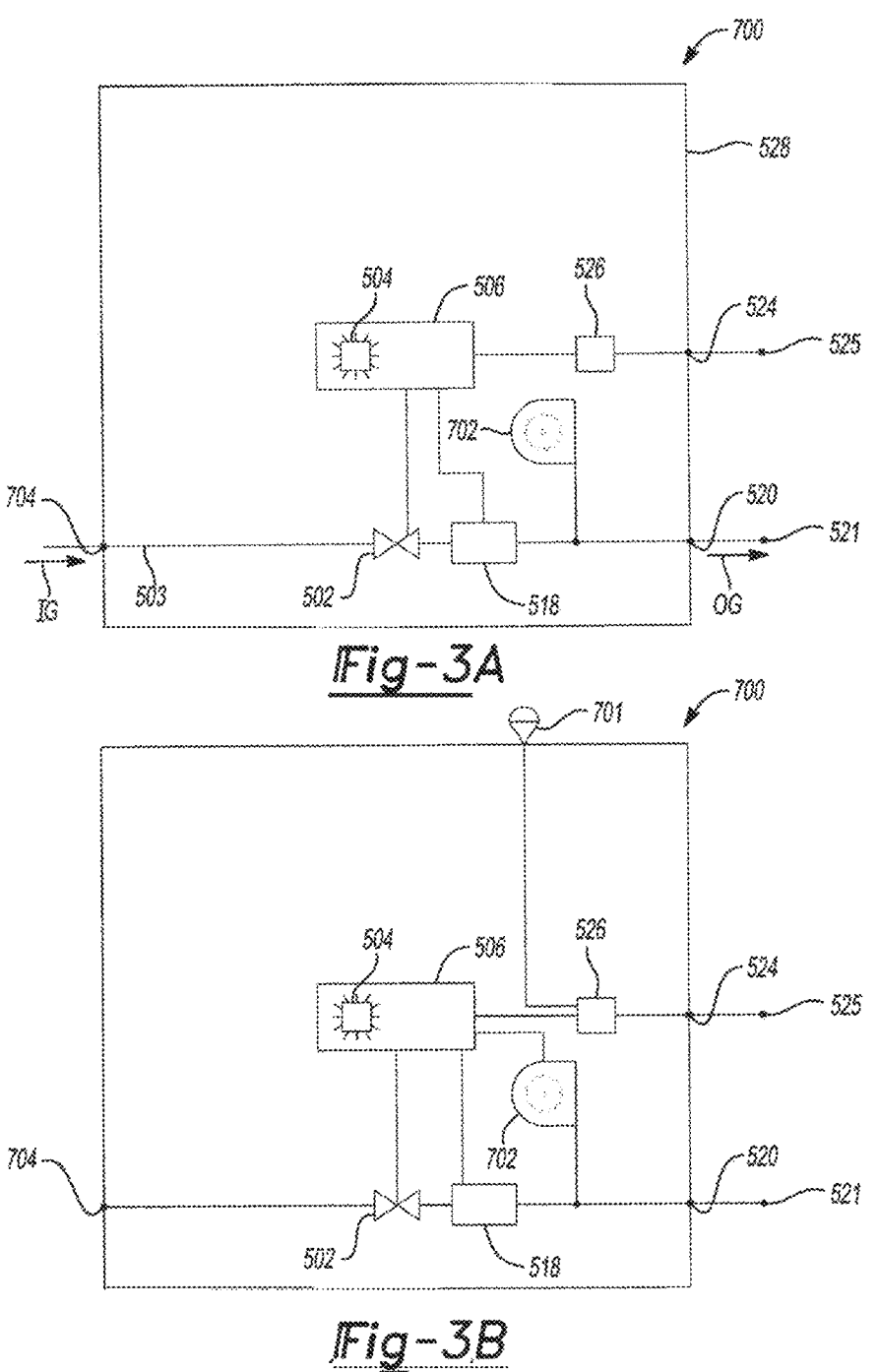
FIG. 3A is a schematic illustration of a ventilator that uses an ultra-low pressure gas source, and a turbine blower configured to add energy to increase the pressure of the gas.
FIG. 3B is a schematic illustration of a ventilator that uses a positive end-expiratory pressure (PEEP) valve.

With reference to FIG. 3A, a ventilator 700 uses one or more ultra-low pressure gas sources. The structure and operation of the ventilator 700 is substantially similar to the structure and operation of the ventilator 500 (FIG. 1) described above, except for the features described below. The ventilator 700 includes a turbine 702 in fluid communication with the tubing 503. The turbine 702 adds energy to increase the pressure of the output gas OG, thereby allowing the flow restrictions to be minimized. In this embodiment, the ventilator 700 does not necessarily include an air entrainment device because of the presence of the turbine 702. Due to the turbine 702, the ventilator 700 can use smaller tubing patient interfaces (e.g., the flow outlet airline 520 and the breath detection airline 524). In other CPAP devices and ventilators, large bore breathing tubing (e.g., 22 mm diameter tubing) are used due to the low pressure gas output, which generally ranges from 4-20 cm $H_2O$ pressure. In some cases, this air entrainment ratio can exceed 25 times the amount of volume/flow rate of the input gas flow. Oxygen concentrators or generation devices can be used to generate ultra-low oxygen output pressures in order to minimize the energy consumption of the gas separation process. Assuming 2 LPM oxygen gas is produced at 0.6 PSIG output pressure and 49 LPM of air entrainment, this would result in a total pressure for the air-$O_2$ mixture of 0.024 PSIG. Based on flow coefficient calculations, this would mean only 32.35 LPM of gas with a 0.024 PSI pressure differential can flow through a 10 mm circular patient interface orifice. Hence, if a discreet and small bore tubing were to be used as the patient interface, for example with a dual lumen nasal cannula or oxygen eyeglass frames with nasal pillows, either lower amounts of air entrainment or higher pressure oxygen gas would be required for the patient interface to be feasible. Hence, in the ventilator 700, the turbine 702 is used to increase the pressure of the input gas IG in the oxygen from an oxygen concentrator (not shown) or gas source from an inlet 704 that is in fluid communication with the ventilator tubing 503. To do so, the turbine 702 is downstream of the valve 502 and the flow sensor 518. The valve 502 is in fluid communication with the ventilator tubing 503. The input gas IG flowing from inlet 704 flows through a valve 502 (e.g., a solenoid valve) and is measured by the flow sensor 518. The input gas IG from inlet 704 flows through the air entrainment device, and then flows to the turbine 702. Hence, the pressure of the air-$O_2$ mixture is increased by adding energy into the ventilator 700. For example, if the pressure of the air-$O_2$ gas mixture increases from 0.024 PSIG to 0.146 PSIG, then 19.7 LPM of gas can flow through ventilator tubing 503 with a 2.4 mm2 orifice cross sectional area. This would make, for example, a pair of discreet oxygen eyeglasses that utilizes two separate 1.2 mm diameter by 2 mm oval air channels feasible with 40 LPM of flow through the patient circuit.

In some embodiments as shown in FIG. 3B, the ventilator 700 can include a positive end-expiratory pressure (PEEP) valve 701. The PEEP valve 701 is in direct fluid communication with the breath detection airline 524. In the present disclosure, term "PEEP valve" means a spring loaded valve that receives the pressure of the patient's exhalation to open and close. In other words, the pressure of the patient's exhalations acts on the PEEP valve 701, causing the PEEP valve 701 to open or close. Specifically, the PEEP valve 701 is configured to close when the pressure of the patient's exhalation is equal to or less than a predetermined pressure threshold to retain exhalation volume in the lungs. In doing so, the PEEP valve 701 increases the volume of gas remaining in the lungs at the end of expiration of the user of the ventilator 700 in order to decrease the shunting of blood through the lungs and improve gas exchange. When the pressure of the patient's exhalation is greater than the predetermined pressure threshold, the PEEP valve 701 opens. In order for the PEEP valve 701 to open and close at appropriate pressure as discussed above, the PEEP valve 701 can be in direct fluid communication with the breath detection airline 524. The PEEP valve 701 can be disposed outside the enclosure 528 to facilitate expunging exhalation gases from the user of the ventilator 700.

In some embodiments as shown in FIG. 3C, the ventilator 700 can include an internal oxygen concentrator 708, which can be fluidly connected to allow external gas sources. This internal oxygen concentrator 708 is disposed inside the enclosure 528 to minimize the size of the ventilator 700. The oxygen concentrator 708 can be of several types, such as, but not limited to: pressure swing adsorption, vacuum pressure swing adsorption, ultra-rapid pressure swing adsorption, oscillator pressure swing adsorption, "molecular gate" pressure swing adsorption, thermally cycled pressure swing adsorption, thermal swing adsorption, Joule-Thomson liquefaction units for the production of liquid oxygen from atmospheric air, gaseous oxygen tanks, liquid oxygen tanks, membrane based gas separation units, and combinations thereof. By using the oxygen concentrator 708, the oxygen percentage supplied to the user of the ventilator 700 can be maximized. The oxygen concentrator 708 is downstream of the valve 502 and upstream of the flow sensor 518 and the turbine 702 to maximize the oxygen supplied to the user of the ventilator 500.

Figure 4:
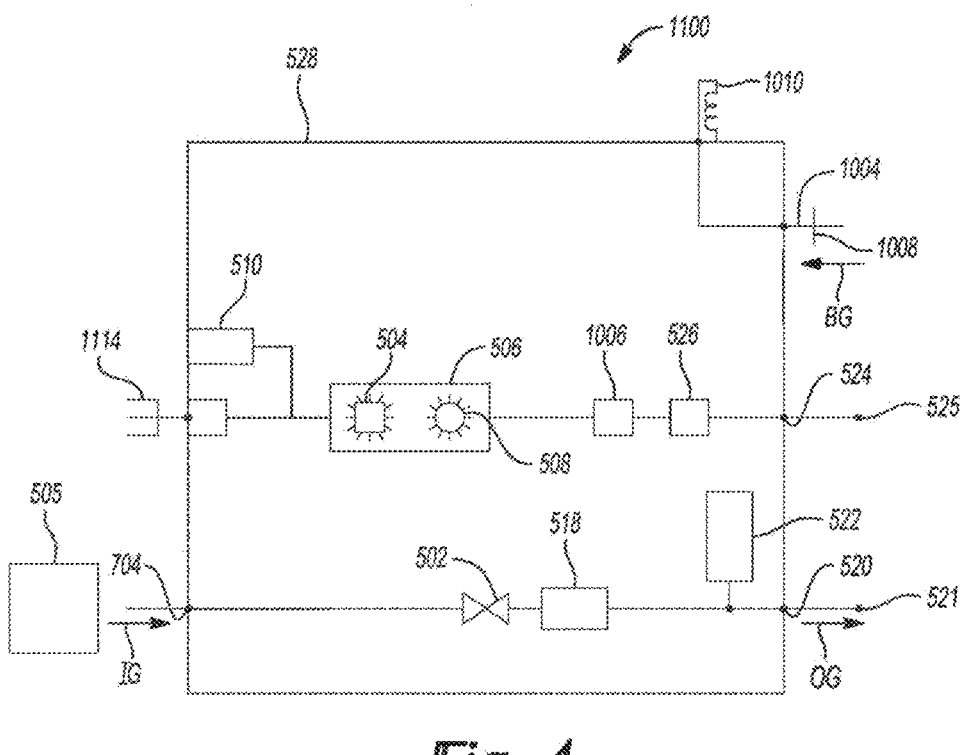
FIG. 4 is a schematic diagram of an invasive ventilator including an exhalation muffler outside the ventilator.

With reference to FIG. 4, a ventilator 1100 is similar to the ventilator 500, except for the features described below. The ventilator 1100 includes an electrical power source 510 (e.g., battery) inside the enclosure 528. The electrical power source 510 is electrically connected to the controller 504. The ventilator 1100 further includes a power receptacle 1114 electrically connected to the electrical power source 510, the controller 504, and the electric board 506. The ventilator 1100 does not include $CO_2$. For invasive ventilation in the configuration shown in FIG. 4, a single limb ventilator circuit would be required. This type of configuration would be more suited for ventilators with a focus on non-invasive home ventilation, where the capability of optional but less frequent use invasive ventilation is desired. This configuration without the active $CO_2$ exhalation valve inside the ventilator 1100 substantially reduces power consumption and weight compared to other ventilators, allowing for lightweight portability with battery power. The ventilator 1100 includes an $CO_2$ exhalation conduit 1004 configured to receive exhalation gas BG from the user. The inlet 704, the flow outlet airline 520, the breath detection airline 524, and the $CO_2$ exhalation conduit 1004 can include tubing connectors. For example, the inlet 704, the flow outlet airline 520, the breath detection airline 524, and the $CO_2$ exhalation conduit 1004 can include quick change connectors such that modifications to the patient circuit and/or gas source can be made, allowing components to be replaced. The $CO_2$ exhalation conduit 1004 is configured to receive exhalation gases from the user. The ventilator 1100 includes the air entrainment device 522, which in some configurations is a fixed $FiO_2$ based on mechanical design and hence should be easy to remove and replace in order for a user to adjust $FiO_2$. The ventilator 1100 includes a bacteria/viral filter 1008 attached to the $CO_2$ exhalation conduit 1004. Patient expired gas flows back through bacteria/viral filter 1008, which includes a 22 mm breathing tube connector to minimize exhalation resistance, before coming into contact with any internal device components. This viral/bacterial filter 1008 can include standard coaxial ISO connectors (ISO 5356-1) that connect to standard breathing tubes using 15 mm ID/22 mm OD connectors for applications in breathing circuits, scavenging circuits, mechanical ventilation, and manual ventilation, including bag valve mask (BVM). This viral/bacterial filter 1008 is designed for single-patient use and, in some embodiments, can have a bidirectional airline, be in-line, low flow resistance of 1.5 cm $H_2O$ pressure at 60 LPM, hydrophobic and electrostatic filtering properties, dead space of 45 mL, and ultrasonically welded. A heat and moisture exchanger (HME) filter or active heated humidification system and/or airline can be added to the flow outlet airline 520 to heat and moisturize the output gas OG output to the patient in order to prevent drying of airways and promote patient health/comfort. Patient gas is expelled to the atmosphere after flowing through bacteria/viral filter 1008 and through an exhaust muffler 1010. The exhaust muffler 1010 is in communication with the $CO_2$ exhalation conduit 1004 and is disposed outside the enclosure 528 to safely expel the $CO_2$ gases.

The ventilator 1100 can include a peak airway pressure sensor 1006 in direct fluid communication with the pressure sensor 526. An LCD screen can indicate, using a graphic or LED bar, when adjustments to gas source input flow should be made based on the peak airway pressure sensor measurements measured by the peak airway pressure sensor 1006. Generally, gas source flow input should be increased when $SpO_2$ saturation is less than 90%, which can be measured using a separate patient/vital signs monitor and/or pulse oximeter and decreased when peak airway pressure is high (i.e., more than 35 cm $H_2O$). A fixed tidal volume delivered per breath can be provided to a user via the LCD screen or via a separate instruction manual based on adjustment of wall $O_2$ supply flow rates. The user can increase tidal volumes delivered to a patient by increasing $O_2$ flow rate input at inlet 704. The inlet 704 can be an input gas source connector and can include a barb fitting, diameter-index safety system (DISS) connectors, quick connectors, and others. For example, the input gas source connector can be a ¼" National Pipe Tapered (NPT) barb fitting that connects to 50 psi hospital wall pipeline $O_2$ supply or $O_2$ tank using ¼" ID oxygen tubing. The inlet 704, the flow outlet airline 520, the breath detection airline 524, and an $CO_2$ exhalation conduit 1004 can include tubing connectors. For example, inlet 704, the flow outlet airline 520, breath detection airline 524, and an $CO_2$ exhalation conduit 1004 can include quick change connectors such that modifications to the patient circuit and/or gas source can be made, allowing components to be replaced. $CO_2$ exhalation conduit 1004 is in direct fluid communication with the $CO_2$ exhalation valve 1002 and is configured to receive exhalation gases from the user. The ventilator 1100 includes the air entrainment device 522, which in some configurations is a fixed $FiO_2$ based on mechanical design and hence should be easy to remove and replace in order for a user to adjust $FiO_2$.

Figure 5:
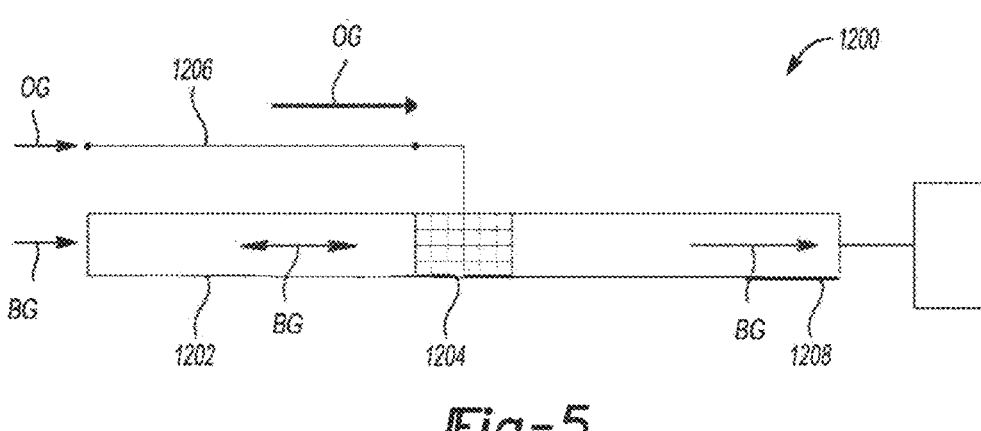
FIG. 5 is a schematic diagram of a non-invasive ventilator circuit using a breathing tube, an adapter, and an oxygen tubing.

With reference to FIG. 5, a non-invasive ventilator circuit 1200 can be connected to the ventilators (e.g., ventilator 500, ventilator 600, ventilator 700, and/or ventilator 1100) or below (e.g., ventilator 1400, ventilator 2100 and/or ventilator 2200) and includes a breathing tubing 1202 (e.g., 22 mm tubing), an adapter 1204, an oxygen tubing 1206, and a patient interface 1208. This breathing tubing 1202 and any other tubing described herein can have various connector and inner tubing diameter sizes not specified in this disclosure. The inlet of the breathing tubing 1202 connects to the breath detection airline to minimize flow resistance and measure breathing pressures (e.g., nasopharynx pressures) accurately without signal interference from the oxygen flow. The breathing tubing 1202 can be connected at the inlet of the tidal volume output airline flow outlet airline 520 and allows bidirectional flow BG. The tidal volume from the ventilator 1100 would be output to the patient in a unidirectional flow from the inlet of the oxygen tubing 1206 to the barb inlet of the adapter 1204, and then to the patient interface 1208 either during a control or assist breath. The adapter 1204 is meant to serve as a connection point for the oxygen tubing 1206 and the breathing tubing 1202, allowing tidal volume flow output to the patient interface 1208 as well as bidirectional breath detection software data measurements using the 22 mm breathing tubing 1202 as a flow conduit to the sensors inside the ventilator, such as a nasopharynx pressure sensor 526 with a pressure measurement range of ±0.018 PSIG. The non-invasive ventilator circuit 1200 is configured to be disposed outside the enclosure 528.

With reference to FIG. 6, an invasive ventilator circuit 1300 for the ventilator 1100 disclosed above or any other ventilator described herein is shown. This invasive ventilator circuit 1300 includes a breathing tubing 1302 (e.g., 22 mm tubing), adapter(s) 1304, 1306, oxygen tubing 1308, breath detection tubing 1310, and a patient interface 1312. This breathing detection tubing 1310 and any other tubing described herein can have various connector and inner tubing diameter sizes not specified in this disclosure. The inlet of the breathing detection tubing 1310 connects to the $CO_2$ exhalation conduit 1004 and/or viral/bacterial filter 1008 to minimize flow resistance during exhalation, which is actively controlled by the ventilator 1100. The breath detection tubing 130 allows bidirectional flow BG. The oxygen tubing 1308 is configured to be connected at the inlet of the flow outlet airline 520. The tidal volume from the ventilator 1100 would be output to the patient in a unidirectional flow from the inlet of the oxygen tubing 1308 to the barb inlet of the adapter 1304, and then to the patient interface 1312 either during a control or assist breath. The bidirectional breath detection software data measurements are taken using the breath detection tubing 1310. The breath detection tubing 1310 is connected to adapter 1306. As such, the breath detection tubing 1310 functions as a flow conduit to the sensors (e.g., pressure sensor 526 and peak airway pressure sensor 1006) inside the ventilator 1000. The adapter 1304, 1306 can be separate or combined into one adapter. These adapter(s) peak airway pressure sensor 1006 serve as a connection point for the oxygen tubing 1308, 22 mm breathing tubing 1302, and breath detection tubing 1310. These adapter(s) 1304, 1306 allow tidal volume flow output to the patient interface 1312 as well as bidirectional breath detection software data measurements and active exhalation control without any sensor signal interference from different simultaneously occurring gas flows, such as breathing flows and/or tidal volume output from the ventilator 1100. The invasive ventilator circuit 1300 is configured to be disposed outside the enclosure 528.

With reference to FIG. 7, a ventilator 1400 includes an internal oxygen concentrator 1402, which can be fluidly connected to external gas sources. This internal oxygen concentrator 1402 is disposed inside the enclosure 528 to minimize the size of the ventilator 1400 and can be of several types, such as, but not limited to: pressure swing adsorption, vacuum pressure swing adsorption, ultra-rapid pressure swing adsorption, oscillator pressure swing adsorption, "molecular gate" pressure swing adsorption, thermally cycled pressure swing adsorption, thermal swing adsorption, Joule-Thomson liquefaction units for the production of liquid oxygen from atmospheric air, gaseous oxygen tanks, liquid oxygen tanks, membrane based gas separation units, and combinations thereof. In a non-limiting example, the internal oxygen concentrator 1402 can be configured as disclosed in U.S. patent application Ser. No. 16/704,413, to which the current disclosure claims priority to, and benefit of, and which is hereby incorporated by reference in its entirety Several of these internal oxygen concentrators 1402 utilize an internal air compressor or blower unit (not shown). The ventilator 1400 can include inlet 704, which can function as an inlet source for gas source. This gas source can additionally include compressed air flow from an external blower or compressor fed to an internal air compressor or blower unit. The internal air compressor can be used to increase the pressure of the inlet gas IG, which either due to the higher flows and/or pressures can potentially increase the potential oxygen production flow rate of the internal oxygen concentrator 1402. This inlet 704 can be in fluid communication with a check valve 1404 to allow the inlet gas IG to be stored in an air volume tank 616. The air volume tank 616 can be external and/or internal to the ventilator 1400. The compressed air (i.e., input gas IG) can be fed directly to the gas separation media such as an adsorbent column. Further, in other embodiments, inlet compressed air can be used to drive a rotor that generates electrical energy to operate the system and/or recharge the batteries in addition to or separately from AC wall outlet electricity. The ventilator 1400 can therefore be pneumatically and/or electrically powered. This can potentially be used to allow the internal oxygen concentrator 1402 to switch between a portable mode, wherein oxygen flow rates of around 5 LPM max are expected, and a stationary mode, where oxygen flow rates of 15 LPM or more can be produced.

The internal oxygen concentrator 1402 can be configured to detect when compressed air or other gas mixture is fed into the ventilator 1400. In response to detecting that the compressed air or other gas mixture is fed into the ventilator 1400, the ventilator 1400 shuts off or reduces the power usage of the internal air compressor, reducing energy consumption of the ventilator 1400 significantly during in-home use. When the oxygen concentrator 1402 is not producing 100% duty cycle continuous flow oxygen output, the air volume tank 616 can be used to store compressed air from either the internal air compressor or external air supply. When oxygen, for example, is not being produced using external compressed air from the inlet gas source, the compressed air can be used to create a Venturi vacuum using a Venturi vacuum generator (not shown) that improves the gas separation performance and/or allows for suctioning the patient using the ventilator 1400. The internal oxygen concentrator 1402 can produce continuous or intermittent flows of oxygen that do not synchronize with the user's breathing. To do so for example, the air volume tank 616 can be used to accumulate produced oxygen. This air volume tank 616 can also be used for sensor measurements, such as for measuring oxygen concentration purity percentage and/or flow rates of the $O_2$ output without using a flow sensor, such as the first flow sensor 518 and/or the second flow sensor 519. In some cases, one or more of the proportional valves 602 are placed upstream of the air volume tank 616 to, for example, implement PI and/or PID flow control of the oxygen gas output. The air entrainment device 522 is used to augment the oxygen output with additional entrained room air, potentially reducing oxygen requirements for the user without requiring the use of an additional and/or separate air blower or compressor for air-$O_2$ mixing as done in other ventilators. The ventilator 1400 can include a separate outlet gas supply airline 1406 such that additional oxygen and/or compressed air can be fed into the ventilator 1400 from an external gas source, including but not limited to: oxygen tanks, portable oxygen concentrators, stationary oxygen concentrators, liquid oxygen tanks, air compressors, and/or air blowers. This separate outlet gas supply airline 1406 can be configured such that the gas accumulates in the air volume tank 616. Then, the air from the air volume tank 616 is received by the air entrainment device 522 and/or is controlled passively for output to the patient by check valves 1408 or actively by electronically controlled valves 502. This output of gas to the user is controllable by breath detection of spontaneous breathing using the breath detection airline 524 and, for example, the pressure sensor 526, and/or via ventilator machine settings such as control breaths for non-spontaneous breathing patients.

FIG. 8 illustrates a ventilator 2100 that can function as a bilevel positive airway pressure (BiPAP) device or continuous positive airway pressure (CPAP) device, oxygen ($O_2$) concentrator, and/or ventilator 2100 with different modes. The ventilator 2100 includes an enclosure 528, a tubing 503 configured to receive the input gas IG, and an internal oxygen concentrator 2102 in fluid communication with the tubing 503. The tubing 503 is entirely or at least partially disposed inside the enclosure 528 to minimize the space occupied by the ventilator 2100. The internal oxygen concentrator 2102 is integrated with the ventilator 2100 and is therefore entirely disposed inside the enclosure 528 to minimize the space occupied by the ventilator 2100. The internal oxygen concentrator 2102 can be used to generate enriched oxygen flow to the patient (i.e., output gas OG). The internal oxygen concentrator 2102 can be turned ON or OFF either automatically using electronic control from the controller 504 (e.g., a microcontroller unit) or via user adjustment of a human-computer interface, including, but not limited to, knobs, touchscreens, and/or switches. The internal oxygen concentrator 2102 can produce and/or deliver oxygen on demand based on a patient's breathing needs, provide a continuous flow of oxygen, and/or produce an oscillatory or irregular oxygen output pattern to the user via the flow outlet airline 520.

The ventilator 2100 can include air entrainment device 522 in fluid communication with the internal oxygen concentrator 2102. The enriched oxygen exiting from the oxygen concentrator 2102 can be used to entrain room air using the air entrainment device 522. The ventilator 2100 can additionally include an air blower 2104 in fluid communication with the internal oxygen concentrator 2102. The air blower 2104 can be in communication with the controller 504. The controller 504 can be programmed to adjust the output gas OG to the patient by the air blower 2104. The air entrainment device 522 could be substituted for or used in combination with the air entrainment device 522 to perform air-$O_2$ mixing. In some embodiments, oxygen could be delivered to the patient during useful phases of respiration as measured using the breath detection airline 524 and the pressure sensor 526. After oxygen is delivered during the useful phase of respiration, a PEEP could be provided using the air blower 2104 to prevent lung collapse in patients with chronic lung diseases, especially those who are mechanically ventilated. This output pressure from the air blower 2104 can be controlled using the controller 504 or via user input from a human-computer interface, at specific ranges for example 0.1-20 cmH₂O pressure. The output flow (e.g., output gas OG) can also be controlled using the controller 504. For example, the controller 504 can control the output gas OG by controlling the blower motor speed of the air blower 2104, voltage, and/or power consumption of the ventilator 2100. In some embodiments, an additional pressure sensor can be added to the outlet airline 520 to measure the output pressure of the output gas OG to the patient.

In some embodiments, the pressure of the output gas OG provided to the patient can be controlled by the controller 504 or the user. The air blower 2104 can control the output airflow (e.g., output gas) to modulate the pressure based on a setpoint. For example, if the output pressure of the $O_2$ and/or compressed air tidal volume from the airline 520 is 6.8 cmH₂O at a flow of 40 LPM and the setpoint is 3.9 cmH₂O, the air blower 2104 can output 1 cmH₂O pressure at 40 LPM flow to achieve the setpoint. In some embodiments of the invention, oxygen pulses could be output intermittently at a frequency greater than an inhalation frequency. In some embodiments, during a period of useful respiration one or more pulse(s) of oxygen could be output followed in terms of timing by one or more pulse(s) of air from the air blower 2104. The lengths of these oxygen and/or blower air pulses can be different or the same as each other.

In another embodiment, the air blower 2104 can be used as an integrated or separate BiPAP/CPAP machine, wherein modes and settings could be selectable, deactivated, and/or activated by the user, healthcare provider, and/or DME based on payment/billing code. For example, the DME supplier can remotely, using software only, enable the ventilator 2100 for use as a non-invasive ventilator if the patient were only prescribed a non-invasive ventilator. If a patient, however, requires supplemental oxygen one year later, the DME can remotely enable this feature using software and then subsequently bill Medicare or an insurance provider for that add-on. In some embodiments, this can also include integrated oxygen and CPAP for obstructive sleep apnea patients with overlap syndrome.

In some embodiments, the blower pressure of the air blower 2104, including IPAP and PEEP, can be controlled by the user, clinician, and/or healthcare provide, with the settings recommended or based on the patient prescription and/or real time physiological characteristics such as breathing, pulse oximetry data, vital signs data, etc. For BiPAP, this generally means that the pressures of the air output can range between 5-20 cmH₂O IPAP, and at least 3 cmH₂O less for PEEP, for example 2-17 cmH₂O PEEP. These IPAP and PEEP variables can be independently or jointly controlled, by the machine software itself, clinician, and/or user. For CPAP or IPAP, the pressure for IPAP and PEEP would be the same. Hence, only one pressure setpoint would be set. In one embodiment, tidal volume and flow rates of the air blower 2104 could also be controlled by the controller 504 (e.g., microprocessor) of the ventilator 2100, a clinician, and/or the user to maximize user comfort, with guidelines based on the patient interface used which could vary from user to user based on patient physiology and mask leakage. This PEEP could also be determined based on peak airway pressure or predicted using the breath detection software. In some embodiments of the invention, the ventilator 2100 can also include wireless communication technology and/or features that allow the ventilator 2100 to function as an at-home sleep test, and/or at-home oxygen test, and provide patient monitoring for the clinician.

With reference to FIG. 9, a ventilator 2200 can utilize Pulse Dose Oxygen Concentrators (POC) 2204 as the input $O_2$ source. Other ventilators can only use high pressure tanks or continuous flow stationary $O_2$ concentrators as pressure sources. This limits the mobility of these other homecare ventilators. In the present disclosure, the ventilator 2200 includes a pressure actuator 2202 that can simulate user breathing to trigger a POC oxygen concentrator 2204. During operation, the pressure actuator 2202 creates a flow ramp that would start at 0 and go past the trigger sensitivity of the $O_2$ conserver device, which can have a −0.20 cmH$_2$O pressure trigger sensitivity. This flow ramp can be optimized based on experimental testing by the manufacturer on different POCs. Hence, a light vacuum force can be generated in order to trigger the $O_2$ conserver. This would be done at a periodic rate, such as 15 breaths or trigger cycles per minute. This periodic rate can be adjusted automatically by the controller 504 of the ventilator 2200 and/or the user via a human-computer interface to avoid the $O_2$ demanded to exceed $O_2$ produced. In some embodiments, the $O_2$ boluses from the POC can accumulate inside an air or oxygen volume tank 516. The oxygen can be stored until delivery to the patient through the valve 602. In some embodiments, these $O_2$ boluses can be measured by internal flow sensor(s) and pressure sensor(s) before accumulation into the air or oxygen volume tank 516. As such, the rate of cycling of the pressure actuator 2202 can be electronically controlled and optimized by the controller 504 based on performance of the POC input at certain breath triggering rates.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware that enable the system, apparatus, structure, article, element, component, or hardware to perform the specified function without further modification. For purposes of this disclosure, a system, apparatus, structure, article, element, component, or hardware described as being "configured to" perform a particular function can additionally or alternatively be described as being "adapted to" and/or as being "operative to" perform that function.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Accordingly, the disclosure and the figures are to be regarded as illustrative rather than restrictive.

What is claimed is:

1. A breathing apparatus, comprising:
a tubing configured to receive an input gas;
a flow outlet airline in fluid communication with the tubing, wherein the flow outlet airline includes an airline outlet, and the flow outlet airline is configured to supply an output gas to a user via the airline outlet;
a breath detection airline with bidirectional airflow during an assisted breath and configured to measure breathing from the user, the breath detection airline comprising an airline inlet configured to receive breathing gas from the user during exhalation by the user, wherein the airline inlet is fluidly separated from the airline outlet of the flow outlet airline to minimize signal interference from a pressure/flow output of fluid that has exited through the airline outlet;
a pressure sensor in direct fluid communication with the breath detection airline, wherein the pressure sensor is configured to measure breathing pressure from the user, and the pressure sensor is configured to generate sensor data indicative of breathing by the user;
a controller in electronic communication with the pressure sensor, wherein the controller is programmed to:
detect the breathing by the user based on the sensor data received from the pressure sensor; and
command the breathing apparatus to provide a flow of the output gas through a breathing tubing connected to the flow outlet airline.

2. The breathing apparatus of claim 1, wherein the controller is further programmed to predict a transition in a breathing time state of the user as a function of the sensor data.

3. The breathing apparatus of claim 1, further comprising a valve in fluid communication with the tubing, wherein the valve is configured to control the flow of the output gas to the user.

4. The breathing apparatus of claim 1, wherein one or more proportional control valves control the flow of inhalation or exhalation gas.

5. The breathing apparatus of claim 1, wherein the breathing apparatus is configured to produce the output gas on demand from an oxygen concentrator or a tank that accumulates the input gas.

6. The breathing apparatus of claim 1, wherein the breathing apparatus further comprises a turbine in a fluid communication with the flow outlet airline, wherein the turbine is configured to increase a pressure of the outlet gas supplied to the user.

7. The breathing apparatus of claim 1, wherein the breathing apparatus further comprises an input gas source in fluid communication with the tubing.

8. The breathing apparatus of claim 7, wherein the breathing apparatus further comprises a valve in fluid communication with the tubing and a flow sensor in fluid communication with the tubing, wherein the input gas source precedes the valve in the flow path.

9. The breathing apparatus of claim 8, wherein the breathing apparatus further comprises a turbine in fluid communication with the flow sensor and the flow outlet airline.

10. The breathing apparatus of claim 9, wherein the breathing apparatus further comprises an enclosure, wherein the tubing, the flow sensor, the flow outlet airline, the valve, and the turbine are disposed inside the enclosure.

11. The breathing apparatus of claim 1, wherein the breathing apparatus further comprises an enclosure, wherein the tubing is disposed inside the enclosure and an exhaust port in direct fluid communication with the breath detection airline is disposed outside the enclosure to facilitate expunging exhalation gases from the user.

12. The breathing apparatus of claim 11, wherein the breathing apparatus further comprises a filter upstream of the exhaust port, wherein the filter is disposed outside the enclosure.

13. The breathing apparatus of claim 12, wherein an electrical power source is disposed inside the enclosure.

14. The breathing apparatus of claim 1, wherein the breathing apparatus further comprises a flow sensor and a valve in fluid communication with the flow sensor, wherein the flow sensor is disposed downstream of the valve.

15. The breathing apparatus of claim 1, wherein the breathing apparatus further comprises an input gas source and a blower in fluid communication with the tubing.

16. The breathing apparatus of claim 1, wherein the breathing apparatus further comprises a blower for which blower pressure can be controlled by the user, a clinician, and/or a healthcare provider, with recommended settings or based on a patient prescription and/or real time physiological characteristics of the user.

17. A ventilator system comprising:
the breathing apparatus of claim 1; and
a non-invasive ventilator circuit, wherein the non-invasive ventilator circuit includes the breathing tubing as a bidirectional flow breathing detection tubing connected to the breath detection airline and the breathing tubing connected to the flow outlet airline via an oxygen tubing connected to an adapter.

18. The ventilator system of claim 17, wherein the non-invasive ventilator circuit includes a patient interface, wherein the adapter connects the oxygen tubing, the breathing tubing, and the patient interface.

19. A breathing apparatus, comprising:
a tubing configured to receive an input gas;
a flow outlet airline in fluid communication with the tubing, wherein the flow outlet airline includes an airline outlet, and the flow outlet airline is configured to supply an output gas to a user via the airline outlet;
a breath detection airline with bidirectional airflow during an assisted breath and configured to measure breathing from the user, the breath detection airline comprising an airline inlet, wherein the airline inlet is fluidly separated from the airline outlet of the flow outlet airline, wherein the breath detection airline is configured to receive breathing gas from the user during exhalation by the user via the airline inlet;

a pressure sensor in direct fluid communication with the breath detection airline, wherein the pressure sensor is configured to measure breathing pressure from the user, and the pressure sensor is configured to generate sensor data indicative of breathing by the user;
a controller in electronic communication with the pressure sensor, wherein the controller is programmed to:
detect the breathing by the user based on the sensor data received from the pressure sensor; and
command the breathing apparatus to provide a flow of the output gas through a breathing tubing connected to the flow outlet airline,
wherein the ventilator further comprises a positive end-expiratory pressure (PEEP) valve in direct fluid communication with the breath detection airline.

20. A ventilator system comprising:
a breathing apparatus, comprising:
a tubing configured to receive an input gas;
a flow outlet airline in fluid communication with the tubing, wherein the flow outlet airline includes an airline outlet, and the flow outlet airline is configured to supply an output gas to a user via the airline outlet;
a breath detection airline with bidirectional airflow during an assisted breath and configured to measure breathing from the user, the breath detection airline comprising an airline inlet, wherein the airline inlet is fluidly separated from the airline outlet of the flow outlet airline, wherein the breath detection airline is configured to receive breathing gas from the user during exhalation by the user via the airline inlet;
a pressure sensor in direct fluid communication with the breath detection airline, wherein the pressure sensor is configured to measure breathing pressure from the user, and the pressure sensor is configured to generate sensor data indicative of breathing by the user; and
a controller in electronic communication with the pressure sensor, wherein the controller is programmed to:
detect the breathing by the user based on the sensor data received from the pressure sensor; and
command the breathing apparatus to provide a flow of the output gas through a breathing tubing connected to the flow outlet airline; and
a ventilator circuit, wherein the circuit includes the breathing tubing, an adapter, a breathing detection tubing, an oxygen tubing, and a patient interface, wherein the breathing detection tubing is directly connected to the adapter, the breathing tubing is directly connected to the adapter, the adapter is directly connected to the patient interface, and the oxygen tubing is directly connected to the adapter.

* * * * *